United States Patent
Lin et al.

(10) Patent No.: US 11,664,094 B2
(45) Date of Patent: May 30, 2023

(54) DRUG-SCREENING SYSTEM AND DRUG-SCREENING METHOD

(71) Applicant: Industrial Technology Research Institute, Hsinchu (TW)

(72) Inventors: Ci-Jie Lin, New Taipei (TW); Chieh-Jen Hsiao, Hsinchu (TW); Chieh-Jen Wang, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 550 days.

(21) Appl. No.: 16/727,858

(22) Filed: Dec. 26, 2019

(65) Prior Publication Data
US 2021/0202049 A1 Jul. 1, 2021

(51) Int. Cl.
| | |
|---|---|
| G16C 20/70 | (2019.01) |
| G06N 3/088 | (2023.01) |
| G16C 20/40 | (2019.01) |
| G06N 3/045 | (2023.01) |

(52) U.S. Cl.
CPC ............. *G16C 20/70* (2019.02); *G06N 3/045* (2023.01); *G06N 3/088* (2013.01); *G16C 20/40* (2019.02)

(58) Field of Classification Search
CPC ...... G16C 20/70; G16C 20/40; G06N 3/0454; G06N 3/088
See application file for complete search history.

(56) References Cited

U.S. PATENT DOCUMENTS

| | | | | |
|---|---|---|---|---|
| 2013/0144887 | A1* | 6/2013 | Chen | G16C 20/70 |
| | | | | 707/748 |
| 2017/0161635 | A1* | 6/2017 | Oono | G06N 7/005 |
| 2019/0010533 | A1* | 1/2019 | Wong | G16B 20/00 |
| 2019/0018933 | A1* | 1/2019 | Oono | G06N 7/08 |
| 2019/0030078 | A1* | 1/2019 | Aliper | A61K 31/192 |

(Continued)

FOREIGN PATENT DOCUMENTS

| | | |
|---|---|---|
| CN | 108647489 A | 10/2018 |
| CN | 108984811 A | 12/2018 |

(Continued)

OTHER PUBLICATIONS

Kadurin et al. (The Cornucopia of Meaningful Leads: Applying Deep Adversarial Autoencoders for New Molecule Development in Oncology, Oncotarget, 2017, vol. 8, (No. 7), pp. 10883-10890) (Year: 2017).*

(Continued)

*Primary Examiner* — Raymond L Nimox (57) ABSTRACT

A drug-screening system includes an encoding module, a candidate-drug generating module and a drug-ranking module. The encoding module is configured to encode a drug expression and at least one drug-ranking indicator to generate a first encoding variable. The candidate-drug generating module is configured to train a generative adversarial network according to the first encoding variable to generate a plurality of candidate drugs, wherein each of the candidate drugs has a generative drug expression and at least one generative drug-ranking indicator. The drug-ranking module is configured to rank strengths of the candidate drugs according to the generative drug-ranking indicator of each of the candidate drugs.

19 Claims, 5 Drawing Sheets

(56) References Cited

U.S. PATENT DOCUMENTS

2019/0050538 A1    2/2019  Luo et al.
2019/0114390 A1*   4/2019  Donner .................. G16B 25/00
2020/0327963 A1*  10/2020  Ul Ain .................. G16H 20/10

FOREIGN PATENT DOCUMENTS

WO    WO2018220368 A1    12/2018
WO    WO2019018693 A2     1/2019

OTHER PUBLICATIONS

Mikechenx "I Code so I Am" (Day 28: Primary School Students Talk About Generative Adversarial Network (GAN), Understanding Neural Network With 100 DIAGRAMS—PART 28 of Concept and Practice Series, Jan. 7, 2018) (Year: 2018).*

Kadurin Artur, et al. "The cornucopia of meaningful leads: Applying deep adversarial autoencoders for new molecule development in oncology," Oncotarget, 2017, pp. 10883-10890, vol. 8, No. 7, Oncotarget, US.

"Generative Adversarial Network, GAN," Dec. 2018, 10 pages, iThome, Taiwan.

Taiwan Patent Office, Office Action, Patent Application Serial No. 109108552, dated Jan. 12, 2021, Taiwan.

Kadurin, Artur et al. "druGAN: an Advanced Generative Adversarial Autoencoder Model for de Novo Generation of New Molecules with Desired Molecular Properties in Silico" Molecular Pharmaceutics, 2017, pp. 3098-3104, ACS Publication, US.

Kadurin, Artur et al. "The cornucopia of meaningful leads: Applying deep adversarial autoencoders for new molecule development in oncology" Oncotarget, Dec. 2017, vol. 8, No. 7, p. 10883-10890, US.

* cited by examiner

FIG. 6

DRUG-SCREENING SYSTEM AND DRUG-SCREENING METHOD

TECHNICAL FIELD

The present disclosure relates to a drug-screening system and a drug-screening method.

BACKGROUND

The process from screening a drug to becoming a truly useful drug may take much time and expense. A lead compound optimization is an important stage in the drug development process, and the average cost of a drug developing process is $414 million (about 23% of the drug development process), and the average time of the drug developing process is two years (about 15% of the drug development process). In the past, optimization models using simulation software or expert experience have been difficult to cope with increasingly complex compound structures, as the design of the simulation software will take much time and the success rate is low.

Accordingly, how to reduce drug development time and cost effectively has become an important issue.

SUMMARY

The present disclosure provides a drug-screening system, which includes an encoding module, a candidate-drug generating module and a drug-ranking module. The encoding module is configured to encode a drug expression and at least one drug-ranking indicator to generate a first encoding variable. The candidate-drug generating module is configured to train a generative adversarial network according to the first encoding variable to generate a plurality of candidate drugs, wherein each of the candidate drugs has a generative drug expression and at least one generative drug-ranking indicator. The drug-ranking module is configured to rank strengths of the candidate drugs according to the generative drug-ranking indicator of each of the candidate drugs.

The present disclosure provides a drug-screening method, which includes the following step. A drug expression and at least one drug-ranking indicator are encoded to generate a first encoding variable. A generative adversarial network is trained according to the first encoding variable to generate a plurality of candidate drugs, wherein each of the candidate drugs has a generative drug expression and at least one generative drug-ranking indicator. The candidate drugs are ranked according to the generative drug-ranking indicator of each of the candidate drugs.

BRIEF DESCRIPTION OF DRAWINGS

The present disclosure can be more fully understood by reading the subsequent detailed description and examples with references made to the accompanying drawings, wherein.

DETAILED DESCRIPTION OF DISCLOSED EMBODIMENTS

Technical terms of the disclosure are based on their general definition in the technical field of the disclosure. If the disclosure describes or explains one or some terms, definition of the terms is based on the description or explanation of the disclosure. Each of the disclosed embodiments has one or more technical features. In possible implementation, a person skilled in the art would selectively implement all or some technical features of any embodiment of the disclosure or selectively combine all or some technical features of the embodiments of the disclosure.

In each of the following embodiments, the same reference number represents the same or a similar element or component.

Figure 1:
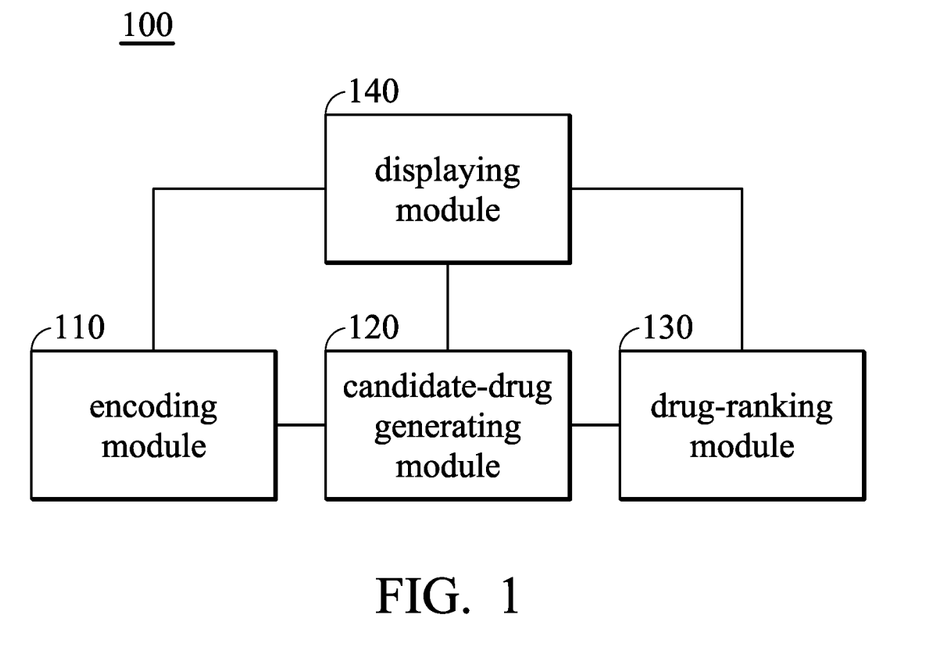
FIG. 1 is a schematic view of a drug-screening system according to an embodiment of the present disclosure.

FIG. 1 is a schematic view of a drug-screening system according to an embodiment of the present disclosure. Please refer to FIG. 1. The drug-screening system 100 includes an encoding module 110, a candidate-drug generating module 120 and a drug-ranking module 130.

Figure 2:
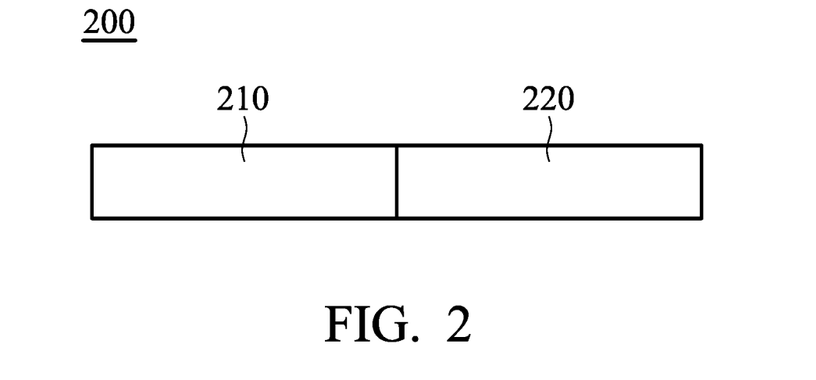
FIG. 2 is a schematic view of encoding variable according to an embodiment of the present disclosure.

The encoding module 110 is configured to encode a drug expression and at least one drug-ranking indicator to generate first encoding variable 200. In the embodiment, the encoding module 110 may be, for example, an encoder. The first encoding variable is, for example, a latent variable, and includes the drug expression and the drug-ranking indicator as shown in FIG. 2. The latent variable may be decoded into the drug expression as a molecular structure of a candidate drug. In FIG. 2, the drug expression is encoded in a region 210 and the drug-ranking indicator is encoded in a region 220 followed the region 210. The drug expression and the drug-ranking indicator may be obtained from a known compound, such as active assays.

In one embodiment, the drug expression includes, for example, a simplified molecular input line entry specification (SMILES) or a compound fingerprint, but the present disclosure is not limited thereto. The SMILES is a specification that explicitly describes the molecular structure in an ASCII string. That is, the SMILES is expressed as a string, such as c1c(O)c1(NC(=O)). The compound fingerprint extracts important structural features from the SMILE. That is, the compound fingerprint is expressed as a vector, such as [1, 1, 0, 1, 0, 0 . . . ]. The drug expression uniquely corresponds to a particular compound (such as a real compound of MCF-7 (Breast Cancer) or other compounds).

Figure 3:
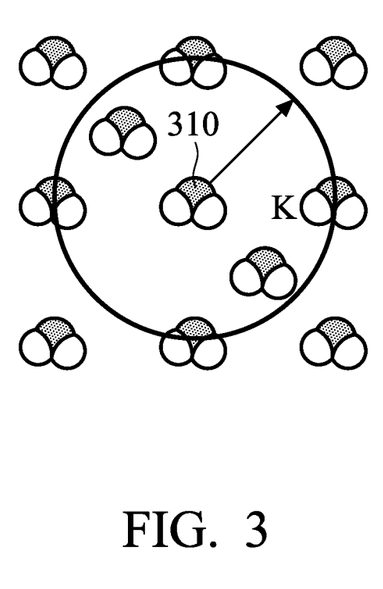
FIG. 3 is a schematic view of a calculation of the drug structure distribution according to an embodiment of the represent disclosure.

In addition, the drug-ranking indicator includes a drug structure distribution or a pharmacological property. In one embodiment, the drug structure distribution may include, for example, a number of nearest neighbor of the compound. For example, as shown in FIG. 3, the similarity between each compound and neighbor nodes is calculated. Then, a number N of the compound located within a similarity threshold K is calculated based on the compound 310. A binarization is performed on the number N of the compound. If N>0, a value of N is set as 1. As shown in FIG. 3, there are six compounds located within the similarity threshold K, and therefore the value of N is 1. Afterward, the value of N serves as the drug structure distribution. In another embodiment, the pharmacological property includes, for example, IC50, GI, etc., but the present disclosure is not limited thereto.

The candidate-drug generating module 120 is coupled to the encoding module 110. In the embodiment, the candidate-drug generating module 120 may be, for example, a microprocessor or a microcontroller. The candidate-drug generating module 120 is configured to train a generative adversarial network (GAN) according to the first encoding variable to generate a plurality of candidate drugs, wherein each of the candidate drugs has a generative drug expression and at least one generative drug-ranking indicator. In the embodiment, the candidate drugs may be, for example, lead compounds. The generative drug expressions respectively include, for example, a simplified molecular input line entry specification (SMILES) or a compound fingerprint, but the present disclosure is not limited thereto. The generative drug-ranking indicators respectively include a drug structure distribution or a pharmacological property. The description of the generative drug expressions and the generative drug-ranking indicators may refer to the description of the drug expressions and the drug-ranking indicator, and the description thereof is not repeated herein.

After the candidate-drug generating module 120 receives the first encoding variable generated by the encoding module 110, the candidate-drug generating module 120 trains the generative adversarial network according to the first encoding variable. For example, the candidate-drug generating module 120 may generate a plurality of fake drug expressions and a plurality of fake drug-ranking indicators according to a random value. In the example, the fake drug expressions and the fake drug-ranking indicators thereof are different from each other. The fake drug expressions respectively include, for example, a simplified molecular input line entry specification (SMILES) or a compound fingerprint, but the present disclosure is not limited thereto. The fake drug-ranking indicators respectively include a drug structure distribution or a pharmacological property. The description of the fake drug expressions and the fake drug-ranking indicators may refer to the description of the drug expressions and the drug-ranking indicator, and the description thereof is not repeated herein.

Then, the candidate-drug generating module 120 may transmit the fake drug expressions and the fake drug-ranking indicators to the encoding module 110. Afterward, The encoding module 110 encodes the fake drug expressions and the fake drug-ranking indicators to generate a plurality of second encoding variables. Then, the encoding module 110 transmits the second encoding variables to the candidate-drug generating module 120. Afterward, the candidate-drug generating module 120 may compare the first encoding variables with the second encoding variables to generate determination values. The determination values indicate the probability of similarities between the drug expression and the drug-ranking indicator included in the first encoding variable with the fake drug expressions and the fake drug-ranking indicators included in the second encoding variables.

Then, the candidate-drug generating module 120 may determine whether the determination values approach a predetermined value. In the embodiment, the predetermined value is, for example, 50%, but the present disclosure is not limited thereto. When it is determined that the determination values approach the predetermined value, this indicates that the determination is converged, and fake drug expressions and the fake drug-ranking indicators in the second encoding variables are similar to the drug expression and the first ranking indicator included in the first encoding variable. Then, the candidate-drug generating module 120 may generate the candidate drugs according to the fake drug expressions and the fake drug-ranking indicators corresponding to the second encoding variables, wherein the generative drug expressions correspond to the fake drug expressions and the generative drug-ranking indicators correspond to the fake drug-ranking indicators.

When it is determined that the determination values do not approach the predetermined value, this indicates that the determination is not converged, and the fake drug expressions and the fake drug-ranking indicators included in the second encoding variables are not similar to the drug expression and the first ranking indicator included in the first encoding variable. Then, the candidate-drug generating module 120 may update the fake drug expressions and the fake drug-ranking indicators. For example, the candidate-drug generating module 120 may modify the fake drug expressions and the fake drug-ranking indicators according to the determination values to update the fake drug expressions and the fake drug-ranking indicators.

Then, the candidate-drug generating module 120 may again transmits the updated fake drug expressions and the updated fake drug-ranking indicators to the encoding module 110. Afterward, the encoding module 110 encodes the updated fake drug expressions and the updated fake drug-ranking indicators to generate the updated second encoding variables. Then, the candidate-drug generating module 120 may compare the first encoding variable with the updated second encoding variables to generate determination values. Afterward, the candidate-drug generating module 120 may again determine whether the determination values approach the predetermined value. Then, the candidate-drug generating module 120 may repeatedly perform the above method until the determination values approach the predetermined value and the candidate-drug generating module 120 generates the candidate drugs according to the fake drug expressions and the fake drug-ranking indicators corresponding to the second encoding information.

The drug-ranking module 130 is coupled to the candidate-drug generating module 120. In the embodiment, the drug-ranking module 130 may be, for example, a microprocessor or a microcontroller. The drug-ranking module 130 is configured to rank strengths of the candidate drugs according to the generative drug-ranking indicator of each of the candidate drugs. That is, when the drug-ranking module 130 receives the candidate drugs, the drug-ranking module 130 may obtain the generative drug expressions and the generative drug-ranking indictors from the candidate drugs.

Then, the drug-ranking module 130 may analyze the generative drug expressions and the generative drug-ranking indictors of the candidate drugs. For example, the drug-ranking module 130 may analyze the strengths of the candidate drugs according to the generative drug-ranking indictors. Then, the drug-ranking module 130 may rank the order of strengths of the candidate drugs according to the strengths of the generative drug-ranking indictors and generates a list of the order of the candidate drugs. Therefore, the embodiment of the present disclosure may effectively reduce drug development time and expense, and accelerate the development process.

Furthermore, the drug-screening system 100 further includes a display module 140. In the embodiment, the display module 140 may be, for example, a display or a monitor, but the present disclosure is not limited thereto. The display module 140 is coupled to the encoding module 110, the candidate-drug generating module 120 and the drug-ranking module 130. The display module 140 is configured to display the first encoding variables, the candidate drugs, the generative drug expressions, the generative drug-ranking indicators and strengths of the candidate drugs through a graphic user interface. Therefore, the user may quickly know the operation of the drug-screening system 100 and the generation of the candidate drugs, thereby effectively reduce the time and expense of drug development, and accelerating the development process.

Figure 4:
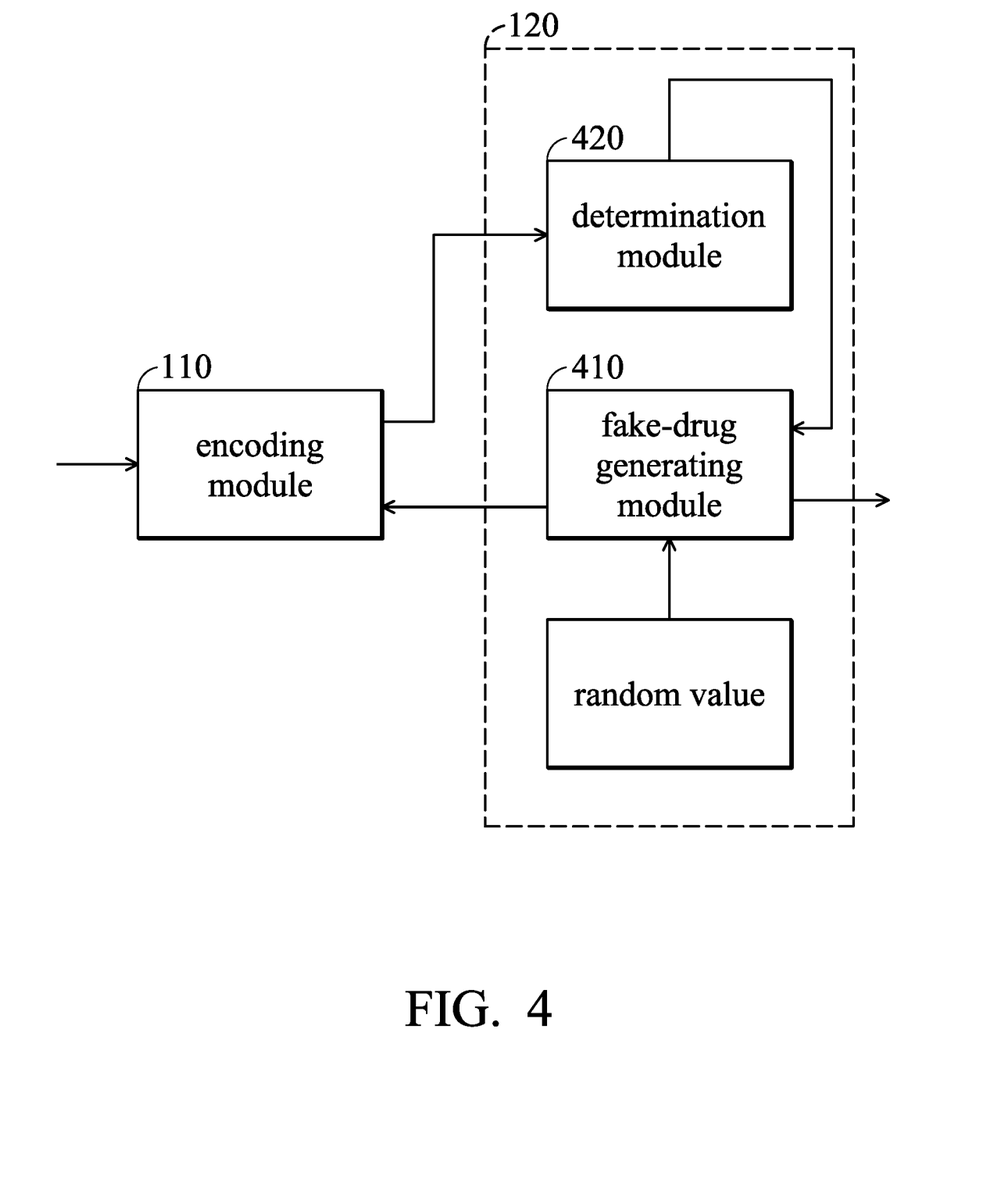
FIG. 4 is a detailed schematic view of the candidate-drug generating module in FIG. 1.

FIG. 4 is a detailed schematic view of the candidate-drug generating module in FIG. 1. Please refer to FIG. 4. In the embodiment, the candidate-drug generating module 120 includes a fake-drug generating module 410 and a determination module 420.

The fake-drug generating module 410 is coupled to the encoding module 110. The fake-drug generating module 410 is configured to generate a plurality of fake drug expressions and a plurality of fake drug-ranking indicators respectively according to a random value. The fake drug expressions and the fake drug-ranking indicators are used to train the generative adversarial network. In the embodiment, the random value may be preset, for example, by the user. Then, the fake-drug generating module 410 transmits the fake drug expressions and the fake drug-ranking indicators to the encoding module 110. Afterward, the encoding module 110 may encode the fake drug expressions and the fake drug-ranking indicators to generate the second encoding variables.

The determination module 420 is coupled to the encoding module 110 and the fake-drug generating module 410. The determination module 420 is configured to receive the first encoding variables and the second encoding variables, and compare the first encoding variable with the second encoding variables to generate determination values.

After the fake-drug generating module 410 receives the determined values, the fake-drug generating module 410 may determine whether the determination values approach a predetermined value. When it is determined that the determination values approach the predetermined value, this indicates that the fake drug expressions and the fake drug-ranking indicators included in the second encoding variables are similar to the drug expression and the drug-ranking indicator included in the first encoding variable. Then, the fake-drug generating module 410 may generate the candidate drugs according to the fake drug expressions and the fake drug-ranking indicators corresponding to the second variables, wherein the generative drug expressions correspond to the fake drug expressions and the generative drug-ranking indicators correspond to the fake drug-ranking indicators.

When it is determined that the determination values do not approach the predetermined value, this indicates that the fake drug expressions and the fake drug-ranking indicators included in the second encoding variables are not similar to the drug expression and the drug-ranking indicator included in the first encoding variable. Then, the fake-drug generating module 410 may update the fake drug expressions and the fake drug-ranking indicators. For example, the fake-drug generating module 410 may modify the fake drug expressions and the fake drug-ranking indicators according to the determination values to update the fake drug expressions and the fake drug-ranking indicators.

Then, the fake-drug generating module 410 may again transmits the updated fake drug expressions and the updated fake drug-ranking indicators to the encoding module 110. Afterward, the encoding module 110 encodes the updated fake drug expressions and the updated fake drug-ranking indicators to generate the updated second encoding variables. Then, the determination module 420 may again compare the first encoding variable with the updated second encoding variables to generate determination values. The determination values may be transmitted to the fake generating module 410. Afterward, the fake-drug generating module 410 may again determine whether the determination values approach the predetermined value. Then, the fake-drug generating module 410 and the determination module 420 may repeatedly perform the above method until the determination values approach the predetermined value and the fake-drug generating module 410 generates the candidate drugs according to the fake drug expressions and the fake drug-ranking indicators.

Furthermore, the fake-drug generating module 410 and the determination module 420 are coupled to the display module 140. Accordingly, the display module 140 may further display the fake drug expressions, the fake drug-ranking indicators, the second encoding variables, the determination values and a comparing result through the graphic user interface. Therefore, the user may quickly know the operation of the drug-screening system 100 and the generation of the candidate drugs, thereby effectively reduce the time and expense of drug development, and accelerating the development process.

Figure 5:
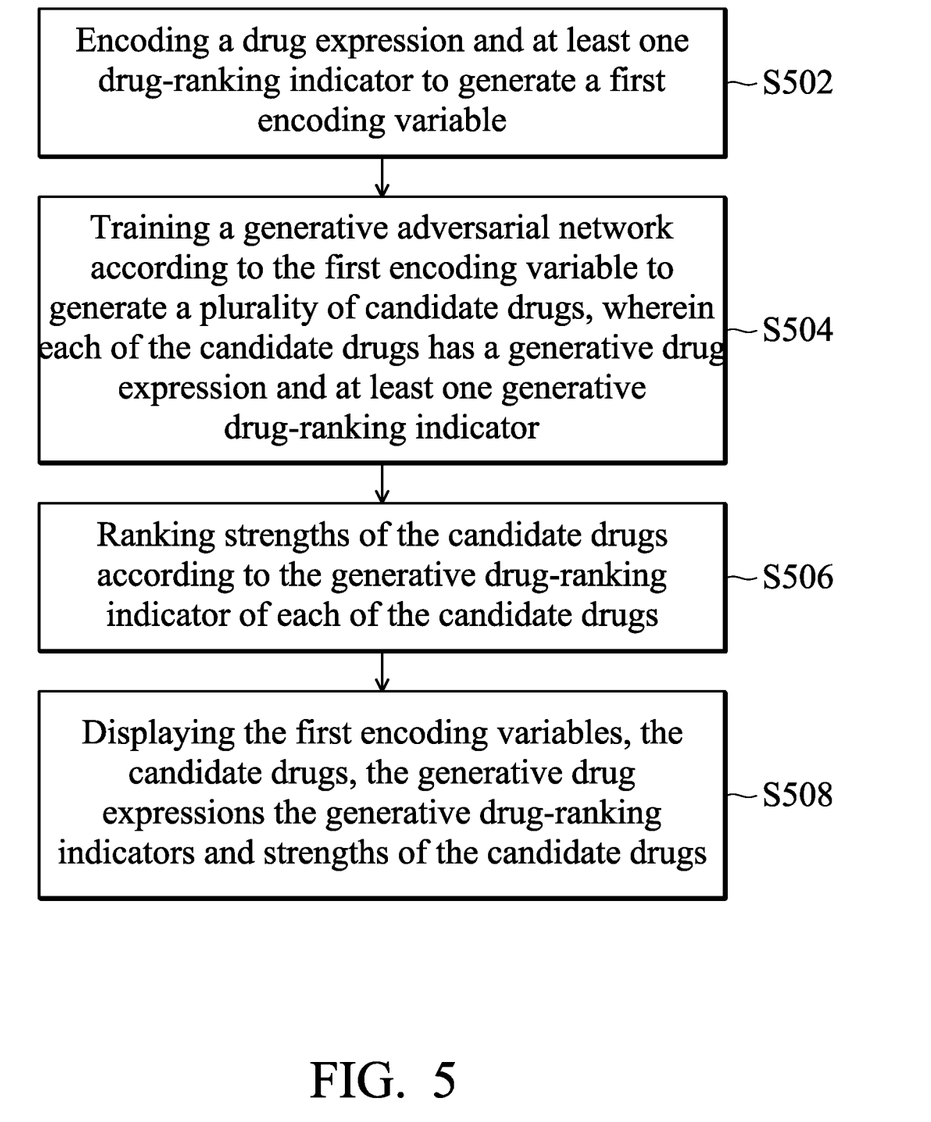
FIG. 5 is a flowchart of a drug-screening method according to an embodiment of the present disclosure.

According to the above-mentioned description, the above embodiments may provide a drug-screening method. FIG. 5 is a flowchart of a drug-screening method according to an embodiment of the present disclosure.

In step S502, the method involves encoding a drug expression and at least one drug-ranking indicator to generate a first encoding variable. In step S504, the method involves training a generative adversarial network according to the first encoding variable to generate a plurality of candidate drugs, wherein each of the candidate drugs has a generative drug expression and at least one generative drug-ranking indicator.

In step S506, the method involves ranking strengths of the candidate drugs according to the generative drug-ranking indicator of each of the candidate drugs. In step S508, the method involves displaying the first encoding variables, the candidate drugs, the generative drug expressions, the generative drug-ranking indicators and strengths of the candidate drugs. In the embodiment, the drug expression and the generative drug expression respectively include a simplified molecular input line entry specification (SMILES) or a fingerprint, but the present disclosure is not limited thereto. In addition, the drug-ranking indicator and the generative drug-ranking indicator include a drug structure distribution or a pharmacological property. The drug structure distribution includes a number of nearest neighbor of a compound, and the pharmacological property includes IC50, GI, but the present disclosure is not limited thereto. Furthermore, the drug expression uniquely corresponds to a particular compound.

Figure 6:
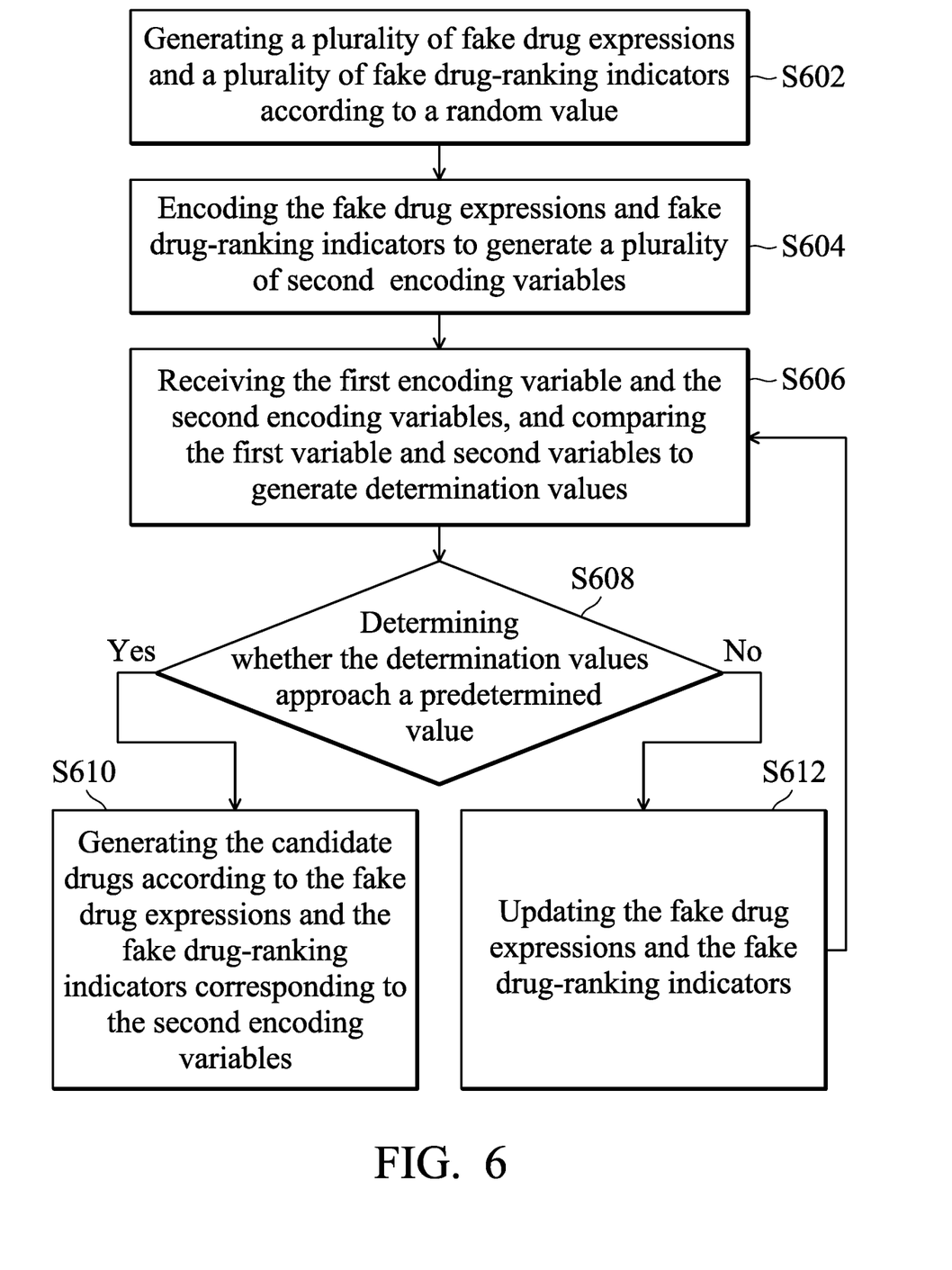
FIG. 6 is a detailed flowchart of step S504 in FIG. 5.

FIG. 6 is a detailed flowchart of step S504 in FIG. 5. In step S602, the method involves generating a plurality of fake drug expressions and a plurality of fake drug-ranking indicators according to a random value. In step S604, the method involves encoding the fake drug expressions and fake drug-ranking indicators to generate a plurality of second encoding variables.

In step S606, the method involves receiving the first encoding variable and the second encoding variables, and comparing the first variable and second variables to generate determination values.

In step S608, the method involves determining whether the determination values approach a predetermined value. When determining that the determination values approach the predetermined value, the method performs step S610. In step S610, the method involves generating the candidate drugs according to the fake drug expressions and the fake drug-ranking indicators corresponding to the second encoding variables.

When determining that the determination values do not approach the predetermined value, the method performs step S612. In step S612, the method involves updating the fake drug expressions and the fake drug-ranking indicators. Then, after step S612 is performed, the method goes to step S606 to compare the drug expression and the drug-ranking indicator with the updated fake drug expressions and the updated fake drug-ranking indicators to generate determination values again. In the embodiment, the fake drug expressions respectively include a simplified molecular input line entry specification (SMILES) or a compound fingerprint, but the present disclosure is not limited thereto. In addition, the fake drug-ranking indicators respectively include a drug structure distribution or a pharmacological property. The drug structure distribution includes a number of nearest neighbor of the compound, and the pharmacological property includes IC50, GI, but the present disclosure is not limited thereto.

In summary, according to the drug-screening system and the drug-screening method of the embodiments of the present disclosure, the drug expression and the drug-ranking indicator are encoded to generate a first encoding variable. The generative adversarial network is trained according to the first encoding variable to generate a plurality of candidate drugs, wherein each of the candidate drugs has a generative drug expression and at least one generative drug-ranking indicator. The candidate drugs are ranked the generative drug-ranking indicator of each of the candidate drugs. Therefore, the embodiment of the present disclosure may effectively reduce the time and expense of drug development, and accelerate the development process.

While the disclosure has been described by way of example and in terms of the embodiments, it should be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A drug-screening system, comprising:
an encoder, configured to encode a drug expression and at least one drug-ranking indicator to generate a first encoding variable, wherein the first encoding variable is a latent variable and comprises the drug expression and the at least one drug-ranking indicator;
a first processor, configured to train a generative adversarial network according to the first encoding variable to generate a plurality of candidate drugs, wherein each of the candidate drugs has a generative drug expression and at least one generative drug-ranking indicator; and
a second processor, configured to rank strengths of the candidate drugs according to the at least one generative drug-ranking indicator of each of the candidate drugs;
wherein the first processor comprises:
a fake-drug generating module, configured to generate a plurality of fake drug expressions and a plurality of fake drug-ranking indicators according to a plurality of random values to the encoder; and
a determination module, configured to receive the first encoding variable and a plurality of second encoding variables, wherein the second encoding variables are generated by the encoder according to the fake drug expressions and the fake drug-ranking indicators, and compare the first encoding variable with the second encoding variables to generate determination values;
wherein the fake-drug generating module determines whether the determination values approach a predetermined value, and when determining that the determination values approach the predetermined value, the fake-drug generating module generates the candidate drugs according to the fake drug expressions and the fake drug-ranking indicators corresponding to the second encoding variables, and when determining that the determination values do not approach the predetermined value, the fake-drug generating module updates the fake drug expressions and the fake drug-ranking indicators.

2. The drug-screening system as claimed in claim 1, wherein the drug expression comprises a simplified molecular input line entry specification (SMILES) or a compound fingerprint, and the generative drug expression comprises the SMILES or a compound fingerprint.

3. The drug-screening system as claimed in claim 1, wherein the at least one drug-ranking indicator and the at least one generative drug-ranking indicator respectively comprise a drug structure distribution or a pharmacological property.

4. The drug-screening system as claimed in claim 3, wherein the drug structure distribution comprises a number of nearest neighbor of a compound, and the pharmacological property comprises IC50, GI.

5. The drug-screening system as claimed in claim 1, wherein the fake drug expressions comprise a simplified molecular input line entry specification (SMILES) or a compound fingerprint.

6. The drug-screening system as claimed in claim 1, wherein the fake drug-ranking indicators comprise a drug structure distribution or a pharmacological property.

7. The drug-screening system as claimed in claim 6, wherein the drug structure distribution comprises a number of nearest neighbor of a compound, and the pharmacological property comprises IC50, GI.

8. The drug-screening system as claimed in claim 1, wherein the drug expression uniquely corresponds to a particular compound.

9. The drug-screening system as claimed in claim 1, further comprising:
a display, coupled to the encoder, the first processor, and the second processor, and configured to display the first encoding variables, the candidate drugs, the generative drug expressions the generative drug-ranking indicators and strengths of the candidate drugs.

10. A drug-screening method, comprising:
encoding a drug expression and at least one drug-ranking indicator to generate a first encoding variable, wherein the first encoding variable is a latent variable and comprises the drug expression and the at least one drug-ranking indicator;
training a generative adversarial network according to the first encoding variable to generate a plurality of candidate drugs, wherein each of the candidate drugs has a generative drug expression and at least one generative drug-ranking indicator; and
ranking strengths of the candidate drugs according to the at least one generative drug-ranking indicator of each of the candidate drugs;

wherein the step of training the generative adversarial network according to the first encoding variable to generate the plurality of candidate drugs comprises:
generating a plurality of fake drug expressions and a plurality of fake drug-ranking indicators according to a plurality of random values;
encoding the fake drug expressions and fake drug-ranking indicators to generate a plurality of second encoding variables;
receiving the first encoding variable and the second encoding variables, and comparing the first variable and second variables to generate determination values;
determining whether the determination values approach a predetermined value;
generating the candidate drugs according to the fake drug expressions and the fake drug-ranking indicators corresponding to the second encoding variables when determining that the determination values approach the predetermined value; and
updating the fake drug expressions and the fake drug-ranking indicators when determining that the determination values do not approach the predetermined value.

11. The drug-screening method as claimed in claim 10, wherein the drug expression comprises a simplified molecular input line entry specification (SMILES) or a compound fingerprint, and the generative drug expression comprises the SMILES or a compound fingerprint.

12. The drug-screening method as claimed in claim 10, wherein the at least one drug-ranking indicator and the at least one generative drug-ranking indicator respectively comprise a drug structure distribution or a pharmacological property.

13. The drug-screening method as claimed in claim 12, wherein the drug structure distribution comprises a number of nearest neighbor of a compound, and the pharmacological property comprises IC50, GI.

14. The drug-screening method as claimed in claim 10, wherein the fake drug expressions respectively comprise a simplified molecular input line entry specification (SMILES) or a compound fingerprint.

15. The drug-screening method as claimed in claim 10, wherein the fake drug-ranking indicators comprise a drug structure distribution or a pharmacological property.

16. The drug-screening method as claimed in claim 15, wherein the drug structure distribution comprises a number of nearest neighbor of a compound, and the pharmacological property comprises IC50, GI.

17. The drug-screening method as claimed in claim 10, wherein the drug expression uniquely corresponds to a particular compound.

18. The drug-screening method as claimed in claim 10, further comprising:
displaying the first encoding variables, the candidate drugs, the generative drug expressions the generative drug-ranking indicators and strengths of the candidate drugs.

19. The drug-screening system as claimed in claim 3, wherein a similarity between each compound and neighbor nodes is calculated, a number N of the compound located within a similarity threshold is calculated, a binarization is performed on the number N of the compound, and a value of the number N serves as the drug structure distribution.

* * * * *